(12) United States Patent
Lich et al.

(10) Patent No.: US 11,123,447 B2
(45) Date of Patent: Sep. 21, 2021

(54) TOWEL DISINFECTANT APPARATUS

(71) Applicants: Rodney Lich, Middleburg, FL (US); James J Foerster, Graniteville, SC (US)

(72) Inventors: Rodney Lich, Middleburg, FL (US); James J Foerster, Graniteville, SC (US)

( * ) Notice: Subject to any disclaimer, the term of this patent is extended or adjusted under 35 U.S.C. 154(b) by 228 days.

(21) Appl. No.: 16/144,695

(22) Filed: Sep. 27, 2018

(65) Prior Publication Data
US 2020/0101184 A1    Apr. 2, 2020

(51) Int. Cl.
*A61L 2/18* (2006.01)
*A61L 2/24* (2006.01)

(52) U.S. Cl.
CPC .................. *A61L 2/18* (2013.01); *A61L 2/24* (2013.01); *A61L 2202/122* (2013.01); *A61L 2202/14* (2013.01); *A61L 2202/26* (2013.01)

(58) Field of Classification Search
CPC ........ A61L 2/18; A61L 2/24; A61L 2202/122; A61L 2202/14; A61L 2202/26
See application file for complete search history.

(56) References Cited

U.S. PATENT DOCUMENTS

| | | | |
|---|---|---|---|
| 3,839,622 A * | 10/1974 | Mastin | A47K 10/06 219/400 |
| 6,582,654 B1 * | 6/2003 | Kral | A61B 1/123 134/161 |
| 6,796,053 B2 | 9/2004 | Lurie | |
| 8,143,553 B2 | 3/2012 | DeFranco et al. | |
| D675,845 S | 2/2013 | Hukill | |
| 2002/0129514 A1 | 9/2002 | Sharp | |
| 2010/0224615 A1 * | 9/2010 | Gallo | A47K 10/06 219/385 |
| 2013/0153560 A1 | 6/2013 | Lev | |

* cited by examiner

*Primary Examiner* — Sean E Conley
(74) *Attorney, Agent, or Firm* — Law Office of Mitchell Ghaneie, P.A.; Mitchell Ghaneie; Christopher Roberts

(57) ABSTRACT

This invention is an apparatus for disinfecting towels with a biocide while also heating or chilling the towels before and after the towels are used. This invention will be particularly useful for individuals at sporting events, or other events where towels are in demand for wiping away perspiration.

13 Claims, 15 Drawing Sheets

TOWEL DISINFECTANT APPARATUS

BACKGROUND OF THE INVENTION

A. Field of the Invention

This invention relates to disinfecting used towels while also cooling or heating the towels for quick reuse by other individuals.

B. Prior Art

While this invention is described herein as being used within the athletic industry, it can be utilized in a variety of industries such as, but not limited to the hospitality industry. Traditionally, at sporting events, specifically on the side lines for each team competing, the players will use towels, typically stored within an insulated container or cooler, to wipe and remove sweat from their face and extremities. After a towel is used, the towel is placed back into the container without being disinfected or cleaned. The used towel is then reused by other players throughout the sporting event, which is not sanitary.

The present invention is an apparatus that is capable of holding the towels, maintaining a desired temperature for the towels and sanitizing the towels after use. Accordingly, this allows for individuals to safely reuse a towel over the course of a sporting event or other extended period of time.

BRIEF SUMMARY OF THE INVENTION

This invention is a towel disinfectant apparatus that allows for disinfecting one or more towels by applying a biocide to the towels as the towels are contained within the apparatus. Accordingly, there are two compartments that are connected with a series of pipes and hoses, which enable the biocide to travel from one compartment to another. A coiled pipe is provided in the first compartment and a perforated PVC rack is placed in the second compartment.

A water and chlorine dioxide solution is placed at the bottom of the second compartment and ice or heated water is provided in the first compartment around the coils. With the use of a pump, the water and chlorine dioxide solution, also referred herein as a biocide, is drawn from the second compartment through a drain. The pump then forces the biocide through a filter and into the chilled or heated coils within the first compartment. As the solution is brought through the piped coils it is pushed into the PVC rack and out of the perforations within the rack. Once the biocide is forced through the perforations or plurality of holes within the rack, it makes contact with any towels hanging on the rack, thereby sanitizing the towels.

In addition, the biocide may be chilled by providing ice within the first compartment so that the coils are surrounded with the ice. Alternatively, water or another solution or fluid may be used to warm the coils and thereby warm the biocide solution as it passes through the coils.

Once the biocide is applied to a towel or emitted through the plurality of perforations in the rack, it is then filtered to remove dirt, particles and other residues that drip from a used towel after it is placed back on the PCV rack.

This invention is described and claimed in several embodiments that allow for the biocide solution to be chilled and warmed as it passes through the coils.

NUMBERING REFERENCE

Figure 1:
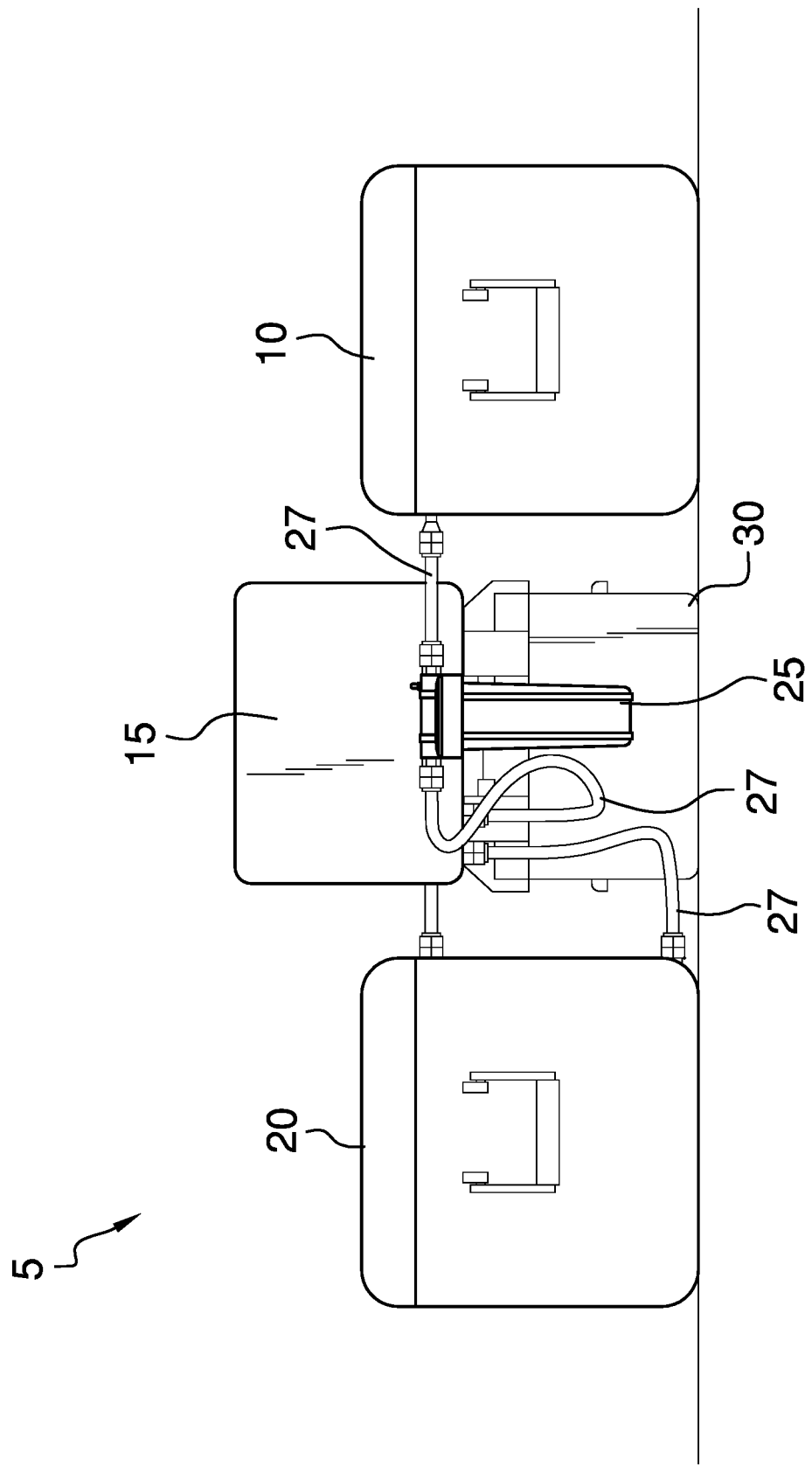
FIG. 1 is a back view of the first embodiment.
Figure 2:
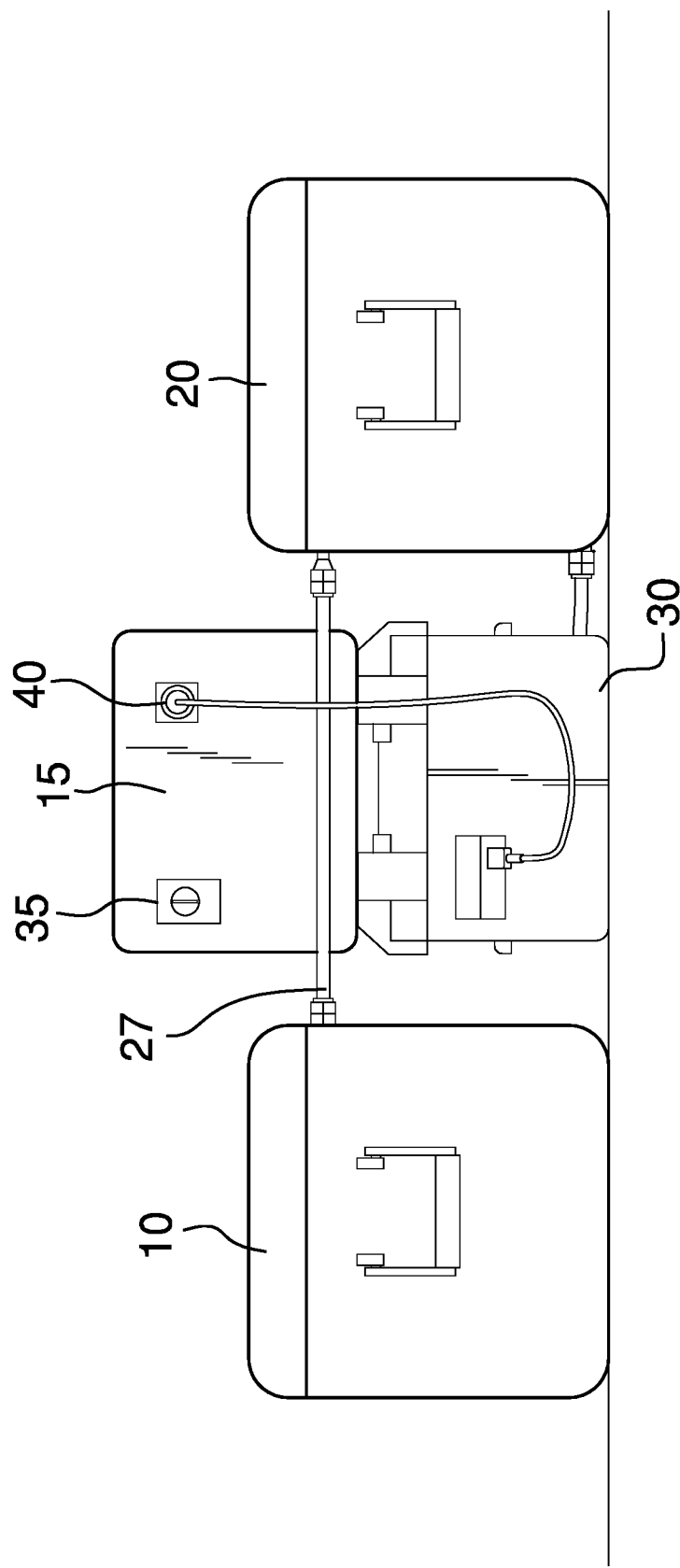
FIG. 2 is a front view of the first embodiment.
Figure 3:
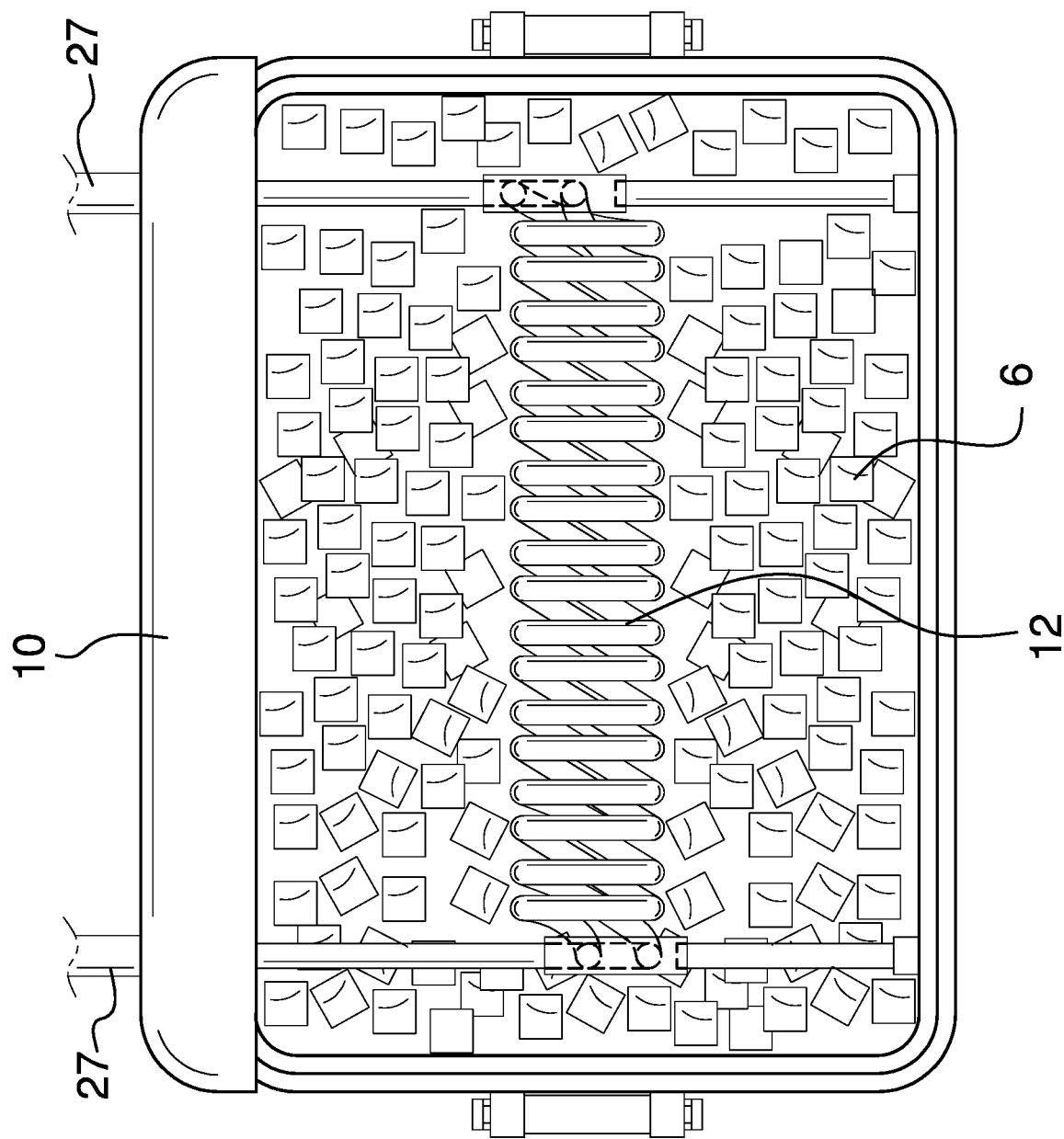
FIG. 3 is a top view of the first compartment of the first embodiment.
Figure 4:
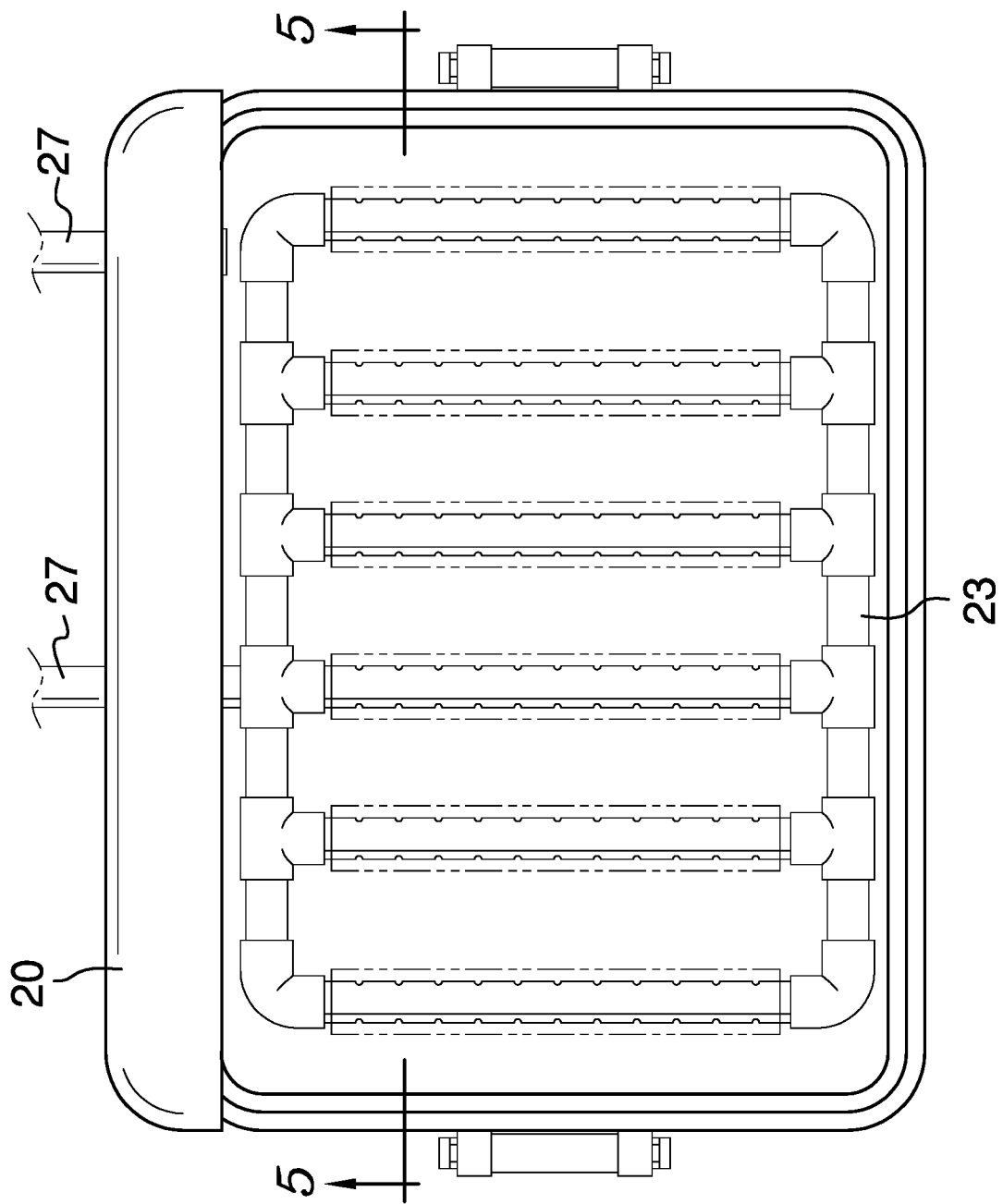
FIG. 4 is a top view of the second compartment of the first embodiment.
Figure 5:
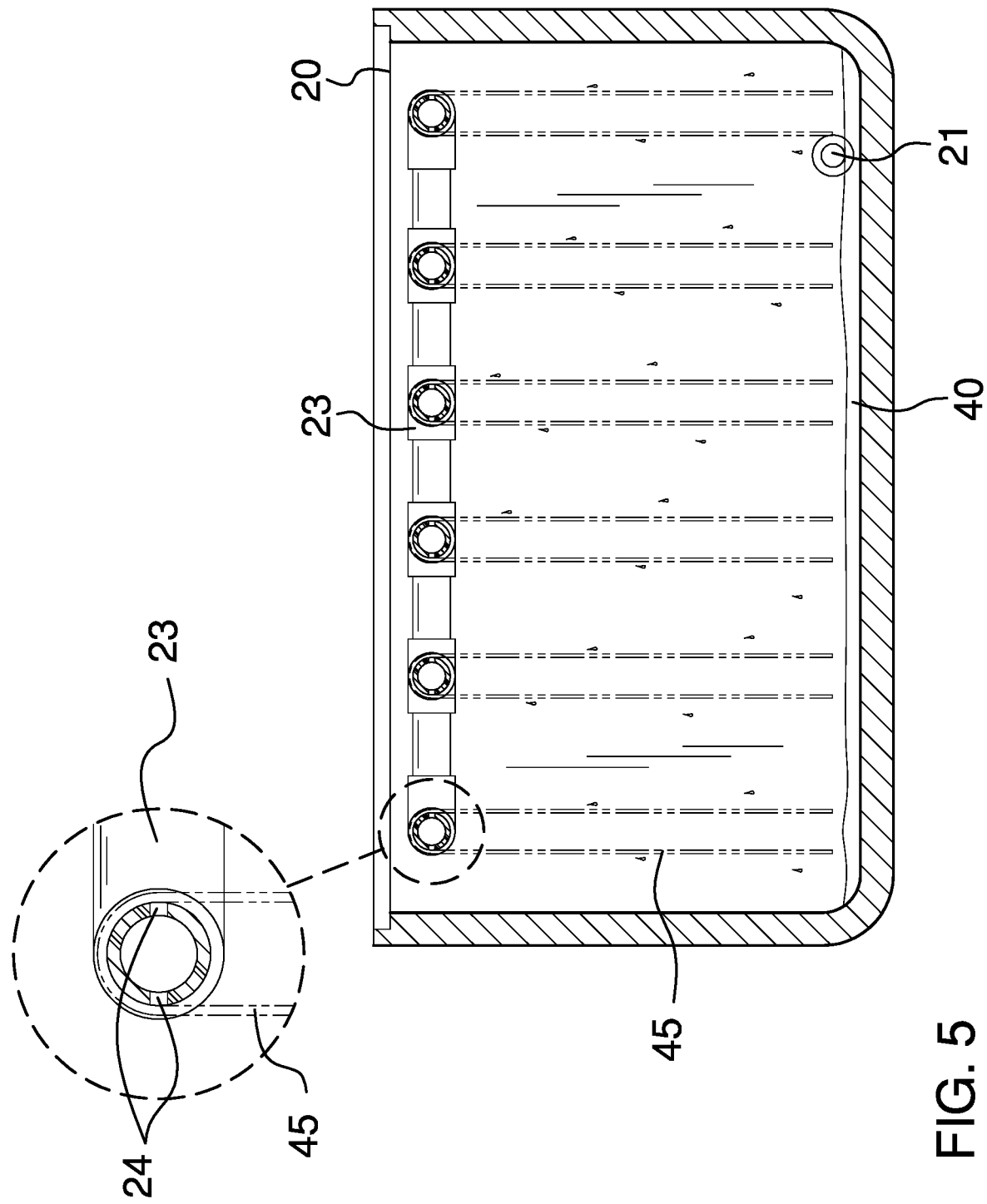
FIG. 5 is a cross-sectional view of the second compartment of the first embodiment.

5—First embodiment
6—Ice
10—First compartment
12—Coiled pipe
15—Pump
20—Second compartment
21—Drain
23—Rack
24—Plurality of perforations
25—Filter
27—Plurality of hoses
30—Battery
35—Pump switch
36—Pump power input
40—Biocide
45—Towel
50—Second embodiment
60—Plurality of heating rods?
70—Gas heating?
80—Plurality of heating plates
90—Tank
100—Third embodiment
125—Single compartment
200—Fourth embodiment
205—Housing
206—Lid
207—Door 208—Plurality of wheels
210—First bay
215—Second bay
220—Third bay
250—Fifth embodiment
254—Handle
255—Housing
256—First lid
257—Second lid
258—Third lid
259—Plurality of wheels
260—First bay
265—Second bay
270—Third bay

DETAILED DESCRIPTION OF THE EMBODIMENTS

This invention is a novel apparatus for disinfecting towels or other articles at a sporting event or other entertainment event and provides at least one compartment, a coiled pipe 12, a rack 23, a pump 15, a drain 21, and a filter 25, a plurality of hoses 27, and biocide 40. While this invention is shown and described in five separate embodiments, there may be modifications made by those of ordinary skill in the art without departing from the underlining concepts described herein. Each embodiment, one through five, will be described respectively below.

First Embodiment

This first embodiment 5 is comprised of a first compartment 10, a second compartment 20, a biocide pump 15, a drain 21, a rack 23, a plurality of perforations 24, a coiled pipe 12, a filter 25, a plurality of hoses 27, and a chilled solution containing a biocide 40. The rack 23 is provided within the second compartment 20 and the coiled pipe 12 is provided within the first compartment 10. The rack 23 is intended to hold towels for use and reuse by one or more individuals. The rack 23 is hollow and constructed of a rigid or semirigid material such as a PVC pipe. However, it is anticipated that the rack 23 may be constructed of a different material, such as, but not limited to, a metal or other plastic material. The biocide 40, or solution containing a biocide 40, will travel within the rack 23 and out of the plurality of perforations 24, which are provided in the rack 23.

Once the biocide 40 exits the plurality of perforations 24, it makes contact with any towels 45 placed on the rack 23. Eventually, after the biocide 40 makes contact with the towels, it will wash dirt and other particles from the towel and drip to the bottom of the second compartment 20 and travel towards and into the drain 21.

The plurality of hoses 27 is provided to allow the biocide 40 to circulate, via the pump 15, from the rack 23 onto one or more towels 45, then down the drain 21 located in the second compartment 20, then through the filter 25, into the coiled pipe 12, which is contained in the first compartment 10 for chilling, and finally back into the rack 23 for further application to the towels 45. Consequently, the towels 45 are continuously sanitized by filtration and reapplication of the biocide 40. It is anticipated that the filter 25 may be positioned within the system so that the biocide 40 can be filtered prior to the heat exchange or alternatively positioned so that the biocide 40 is filtered after the heat exchange. In other words, the filter 25 may be placed on the inlet side or the exit side of the chilled or heated coiled pipes 12 that the biocide 40 is being pumped through.

It is anticipated that a programmable controller (not shown) may be used for controlling the temperature of the biocide 40, the pressure at which it is circulated and pushed through the plurality of perforations 24 within the rack 23, as well as provide remote control over the apparatus.

Second Embodiment

This second embodiment 50 is comprised of a first compartment 10, a second compartment 20, a biocide pump 15, a drain 21, a rack 23, a plurality of perforations 24, a coiled pipe 12, a filter 25, a plurality of hoses 27, and a secondary fluid that is heated by one or more heating elements. The heating element or elements may be provided in the first compartment 10, within the walls of the first compartment 10, or outside of the first compartment 10, which is shown in FIG. 6, FIG. 8, and FIG. 10 and FIG. 12. When the heating elements or elements are activates the secondary fluid is thereby heated, which allows the first compartment 10 to allows for a heat exchange has the biocide passes through the coiled pipe 12. In this embodiment the secondary fluid is described as being water, however it is anticipated that it may be a different liquid compound or solution.

Figure 6:
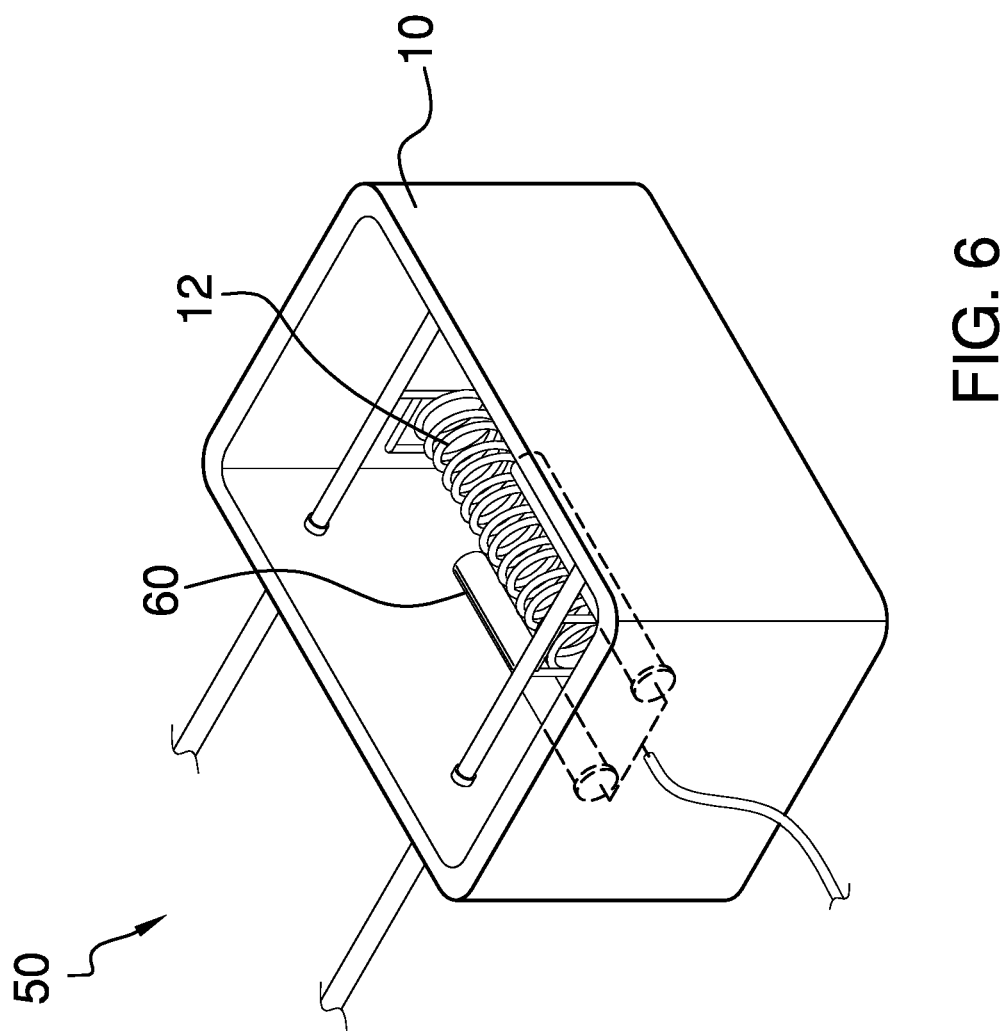
FIG. 6 is an isometric view of a second embodiment wherein a plurality of heating rods is provided in the first compartment for warming the coils.
Figure 7:
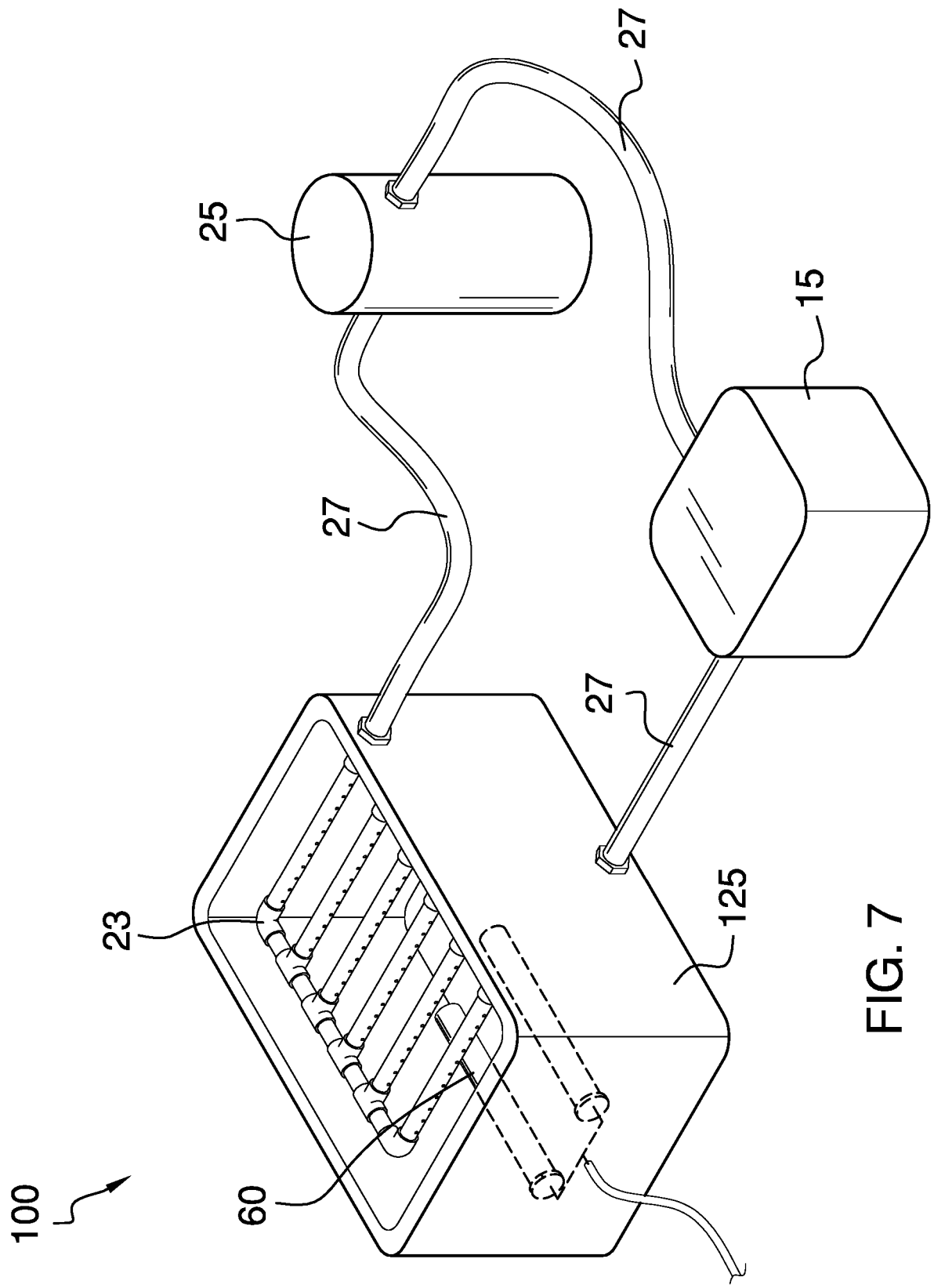
FIG. 7 shows a diagram of a third embodiment wherein the rack and plurality of heating rods are provided in a single compartment.
Figure 8:
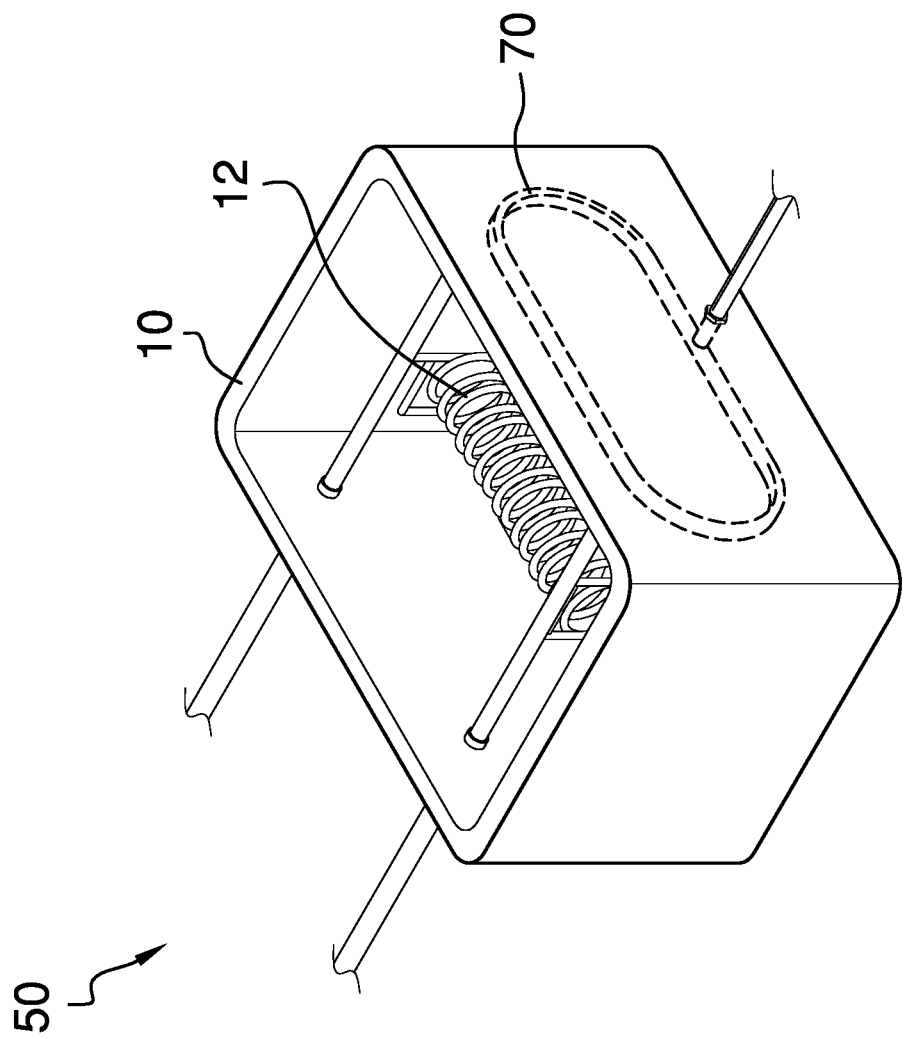
FIG. 8 shows an isometric view of a second embodiment wherein a gaseous fuel sourced heating element is provided.
Figure 9:
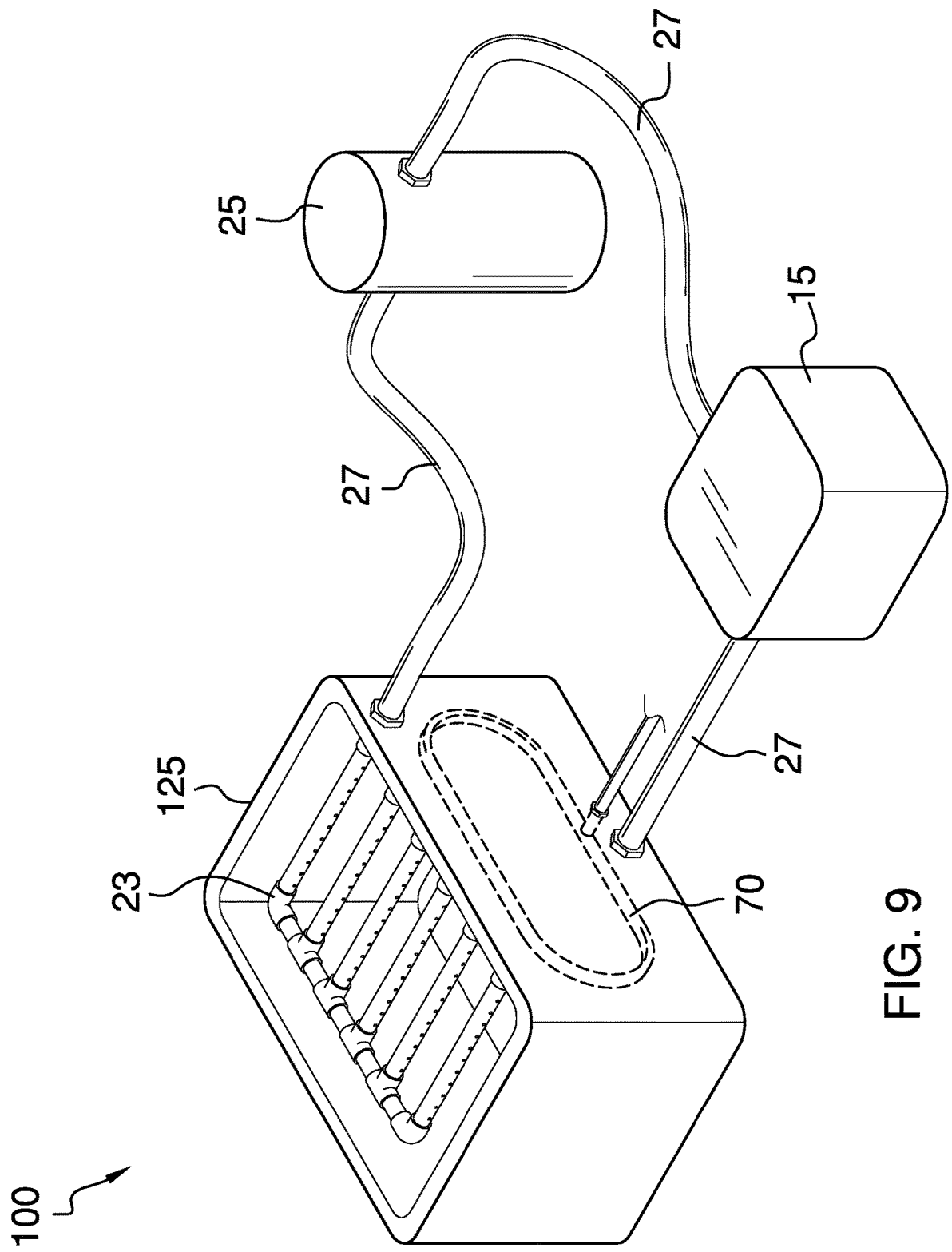
FIG. 9 is a view of the third embodiment wherein the gaseous fuel sourced heating element is used to heat through the walls of the singular compartment.
Figure 10:
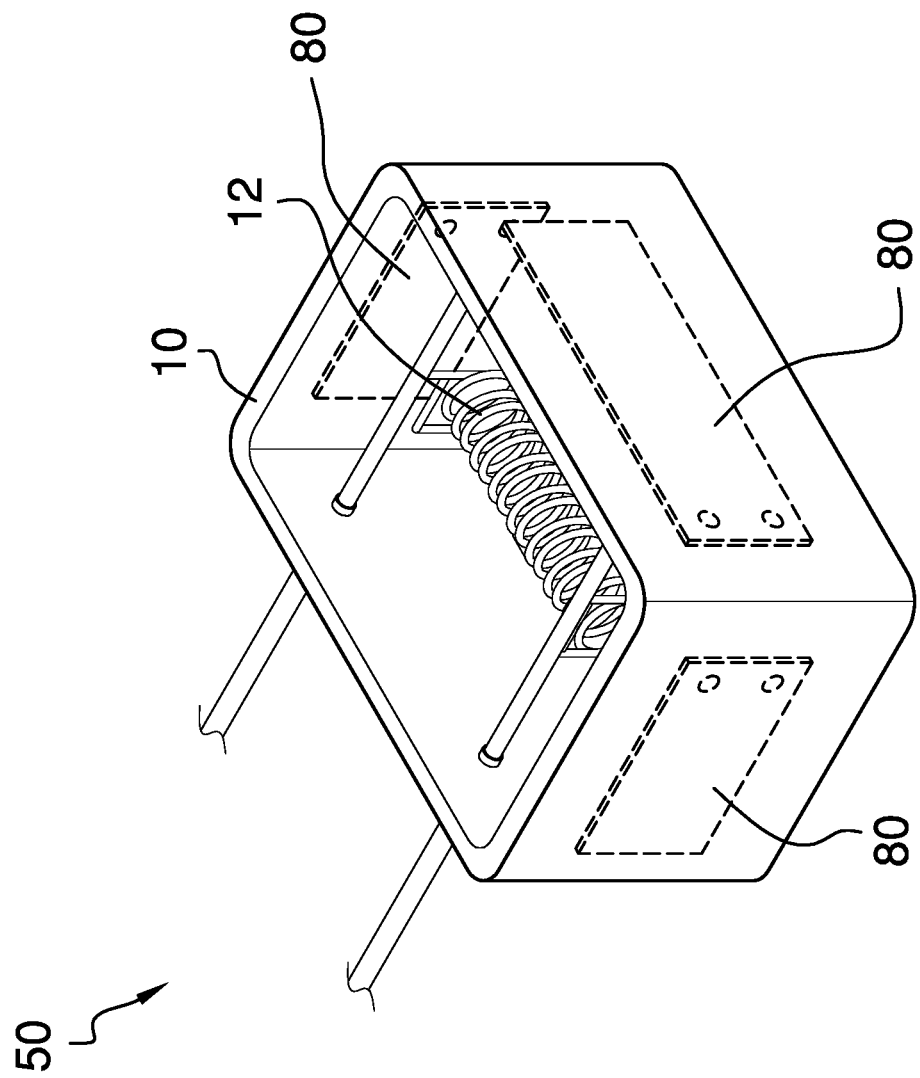
FIG. 10 is a second embodiment wherein a plurality of heating elements are provided within the wall of the first compartment.
Figure 11:
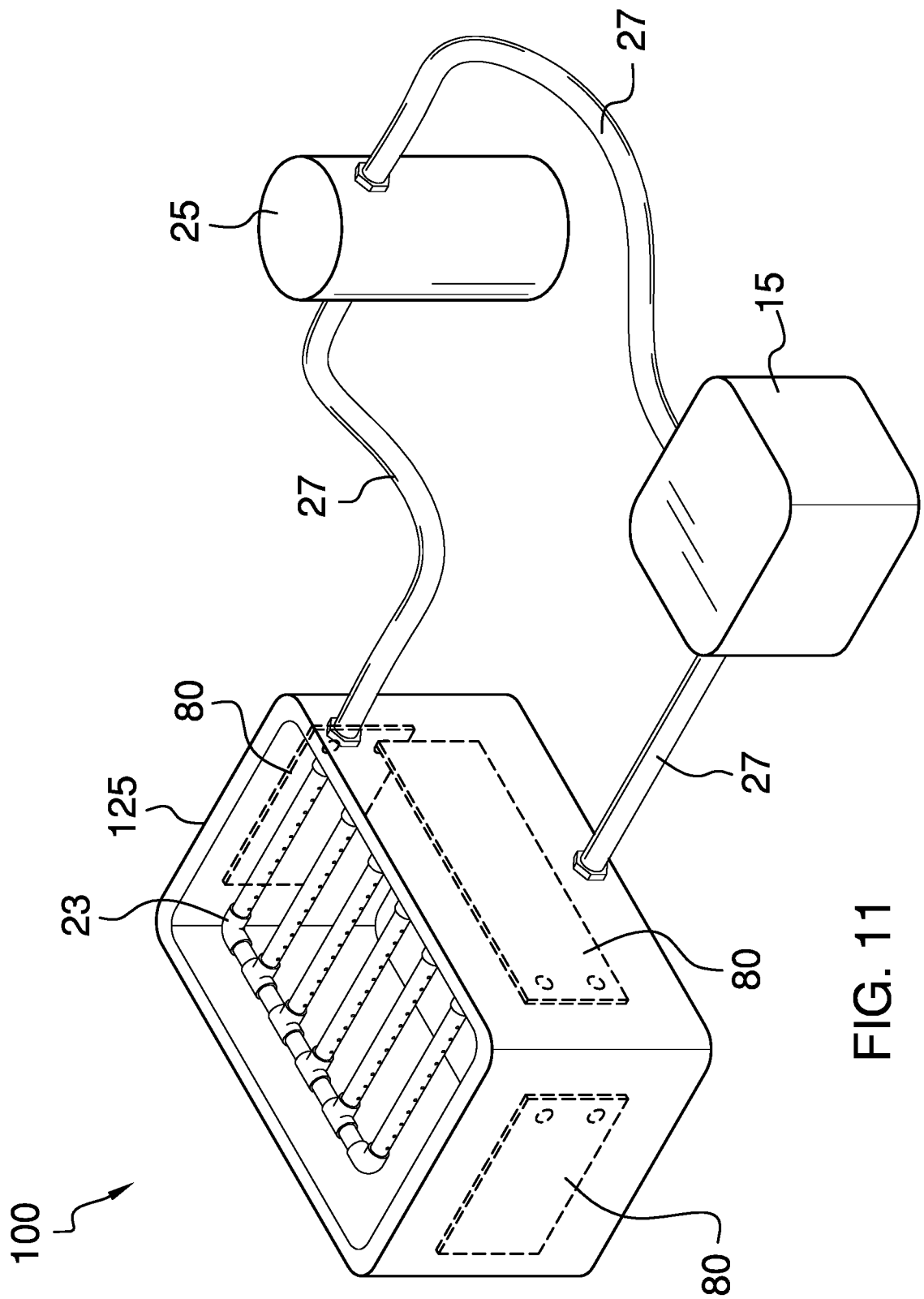
FIG. 11 is a third embodiment wherein a plurality of heating elements are provided within the wall of one compartment that also provides a rack.

In FIG. 6, a plurality of heating rods 60 is provided in the first compartment 10 for heating water or other fluid which surrounds the piped coils 12. In FIG. 8, a gaseous fuel sourced heating apparatus 70 being applied to the walls of the first compartment is shown. Accordingly, as the walls are heated, water or other fluid is warmed, thereby warming the coiled pipes 12, which the biocide 40 passes through. As an alternative to the heating elements shown and described in FIG. 6 and in FIG. 8, a plurality of heating plates 80, shown in FIG. 10, are provided in the wall of the first compartment 10, to assist in heating water within the first compartment 10.

Figure 12:
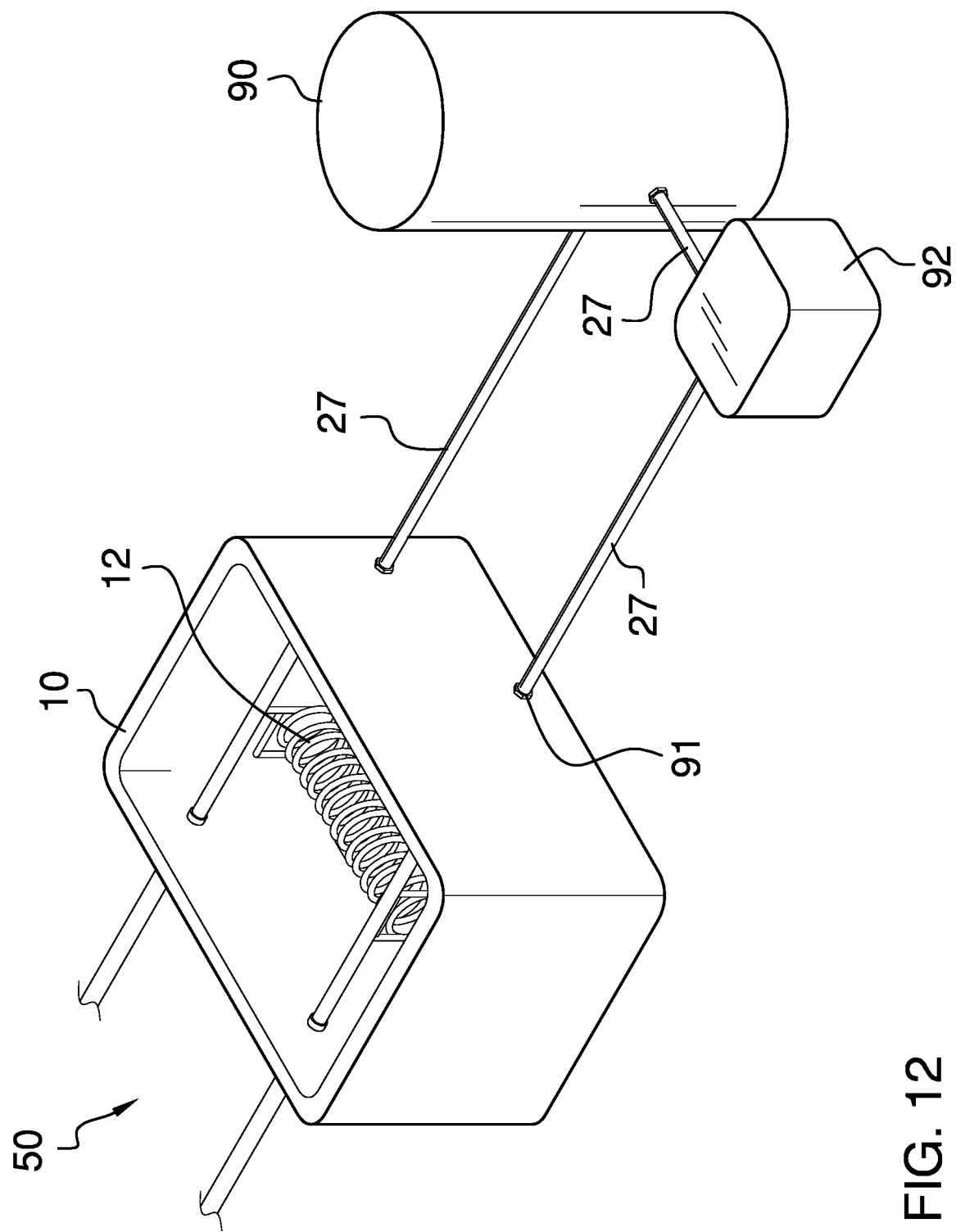
FIG. 12 is a second embodiment wherein a water heater is provided to heat water within the first compartment to warm the biocide solution as it passes through the coils.
Figure 13:
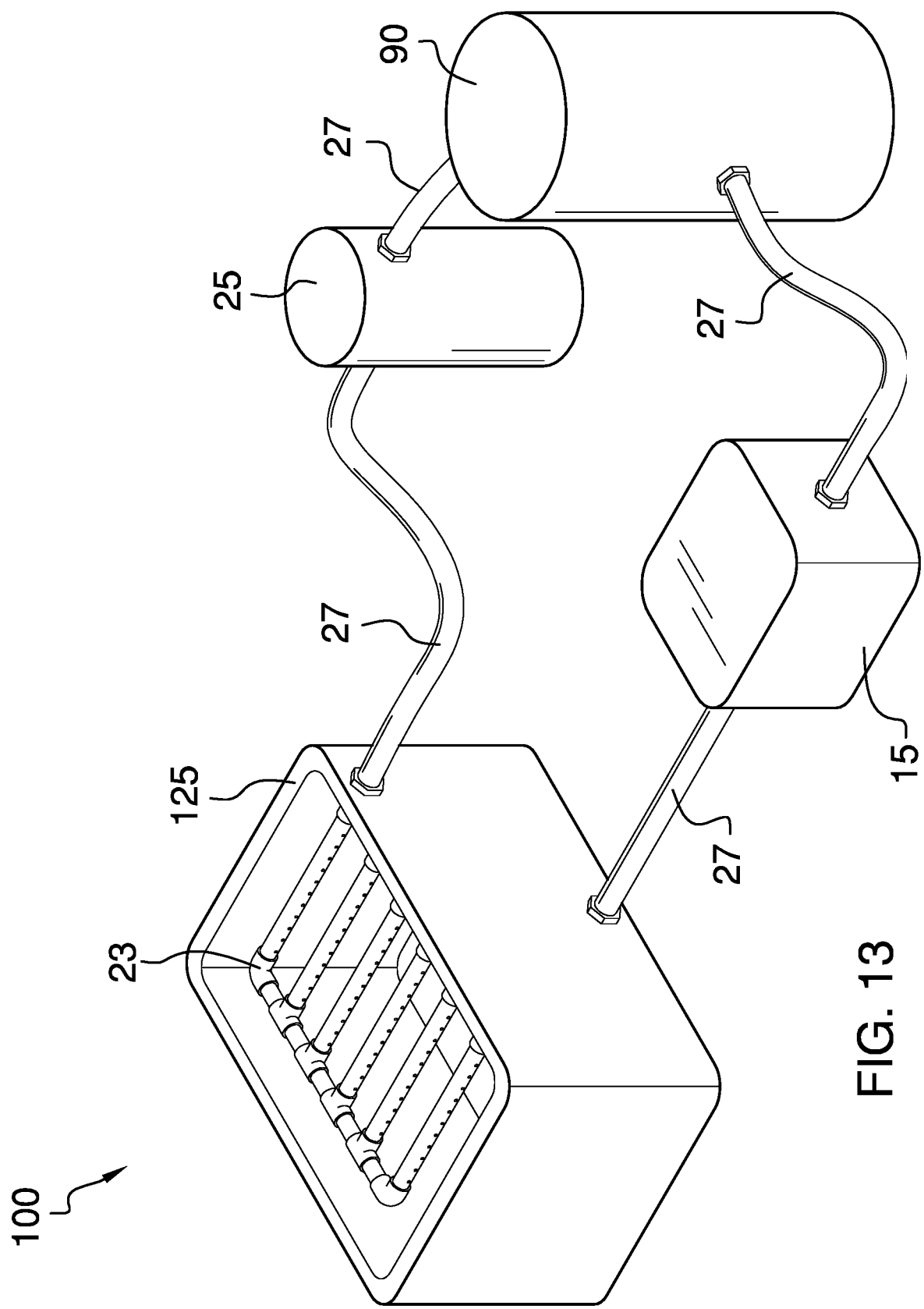
FIG. 13 is a third embodiment wherein a tank is provided to heat the biocide and circulate it into the singular compartment where the towel rack is provided.

As a further alternative, FIG. 12 shows the use of a hot water tank 90 and secondary fluid pump 92, which cycles hot water into the first compartment 10. The secondary fluid pump 92 draws water out of the first compartment 10 through a secondary fluid drain 91 and pushes it into the water tank 90 for heating. The heated water is then released or pumped back into the first compartment 10 to eventually be drawn out again.

It is anticipated that ice 6 may used instead of the heating elements, should the user desire to cool or chill the biocide 40. It is additionally anticipated that the filter 25 may be positioned within the system so that the biocide 40 can be filtered prior to the heat exchange or alternatively positioned so that the biocide 40 is filtered after the heat exchange. In other words, the filter 25 may be placed on the inlet side or the exit side of the chilled or heated coiled pipes 12 that the biocide 40 is being pumped through. It is also anticipated that a programmable controller may be used for controlling the temperature of the biocide 40, the pressure at which it is circulated and pushed through the plurality of perforations 24 within the rack 23, as well as provide remote control over the apparatus.

Third Embodiment

This third embodiment 100 is comprised of a single compartment 125, a pump 15, a drain 21, a rack 23, a plurality perforations 24, a coiled pipe 12, a filter 25, a plurality of hoses 27, a secondary fluid, and at least one heating element. Accordingly, the heating element or plurality of heating elements is provided in the singular compartment 125, within the walls of the compartment 125, or on the outside of the singular compartment 125 which is shown in FIG. 7, FIG. 9, and FIG. 11, and FIG. 13. The heating elements shown in FIG. 7, FIG. 9, FIG. 11, and FIG. 13 are respectively the same heating elements shown in FIG. 6, FIG. 8, FIG. 10 and FIG. 12. However, in this third embodiment, a second compartment and secondary fluid is not required because the biocide 40 makes direct contact with the heating elements of FIG. 7, FIG. 9, FIG. 11, and FIG. 13. Therefore, the singular compartment 125 may provide both, the heat exchange and the biocide 40 application.

It is anticipated that ice 6 may be used instead of the heating elements, should the user desire to cool or chill the biocide 40. It is additionally anticipated that the filter 25 may be positioned within the system so that the biocide 40 can be filtered prior to the heat exchange or alternatively positioned so that the biocide 40 is filtered after the heat exchange. In other words, the filter 25 may be placed on the inlet side or the exit side of the chilled or heated coiled pipes 12 that the biocide 40 is being pumped through. It is also anticipated that a programmable controller may be used for controlling the temperature of the biocide 40, the pressure at which it is circulated and pushed through the plurality of perforations 24 within the rack 23, as well as provide remote control over the apparatus.

Fourth Embodiment

Figure 14:
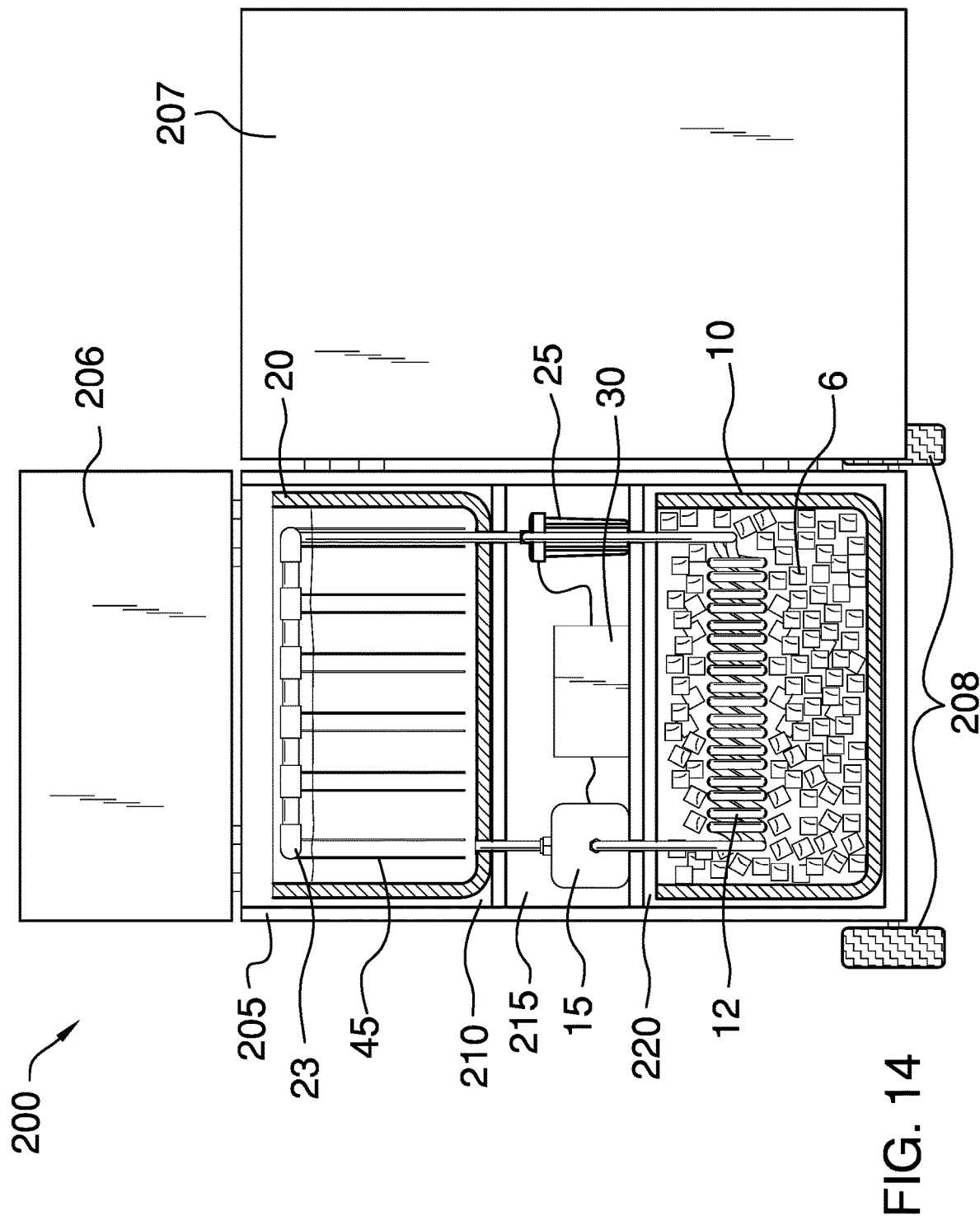
FIG. 14 is a fourth embodiment wherein the first compartment is provided below the second compartment and the entire invention is contained within a housing that provides a top lid and a front door.

This fourth embodiment 200, shown in FIG. 14, is comprised of a housing, a first compartment 10, a second compartment 20, a pump 15, a drain 21, a rack 23, a plurality of perforations 24, a coiled pipe 12, a filter, and a plurality of hoses 27. As described in the first and second embodiments, the rack 23 with the plurality of perforations 24, is placed in the second compartment and the coiled pipe 12 is placed in the first compartment 10. Also, the plurality of hoses connect to the rack 23, the pump 15, the filter 25, the coiled pipe 12, and the second compartment together.

The housing 200 is further comprised of, a top, a bottom, a front, a back, an interior, an exterior, a lid 206, a door 207, a plurality of wheels 208, a first bay 210, a second bay 215, and a third bay 220. Each of the three bays are provided on the interior of the housing, wherein the first bay 210 is placed above the second bay 215 and the second bay is placed above the third bay 220. The lid 206 is provided at the top of the housing 205 above the first bay 210 and the door 207 is provided on the front of the housing 205. The second compartment 20 is provided in the first bay 210, the pump 15 and the filter 25 are provided in the second bay 215, and the first compartment 10 is provided in the third bay 220, which is shown in FIG. 14.

The lid 206 is attached by a hinge to the housing 205 and may be opened or closed. A user may open the lid 206 to obtain direct access to the second compartment 20 as the second compartment 20 is placed in the first bay 210 of the housing. This is to allow users quick and easy access to a sanitized towel 45.

The door 207 is also attached by a hinge to the housing 205 to allow for easy access to the first compartment 10, the second compartment 20, the pump 15, and the filter 20.

Although it is not shown a handle (not shown) may be provided on the back of the housing 205 to assist with moving or rolling the apparatus on its wheels 208 to a desired location. In addition, it is anticipated that this fourth embodiment could be modified so there is only one compartment, where the rack 23 and coiled pipe 12 are provided in a singular compartment 125. It is also anticipated that one or more heating elements can be provided in the first compartment 10. It is further anticipated that the filter 25 may be positioned within the system so that the biocide 40 can be filtered prior to the heat exchange or alternatively positioned so that the biocide 40 is filtered after the heat exchange. In other words, the filter 25 may be placed on the inlet side or the exit side of the chilled or heated coiled pipes 12 that the biocide 40 is being pumped through.

Fifth Embodiment

Figure 15:
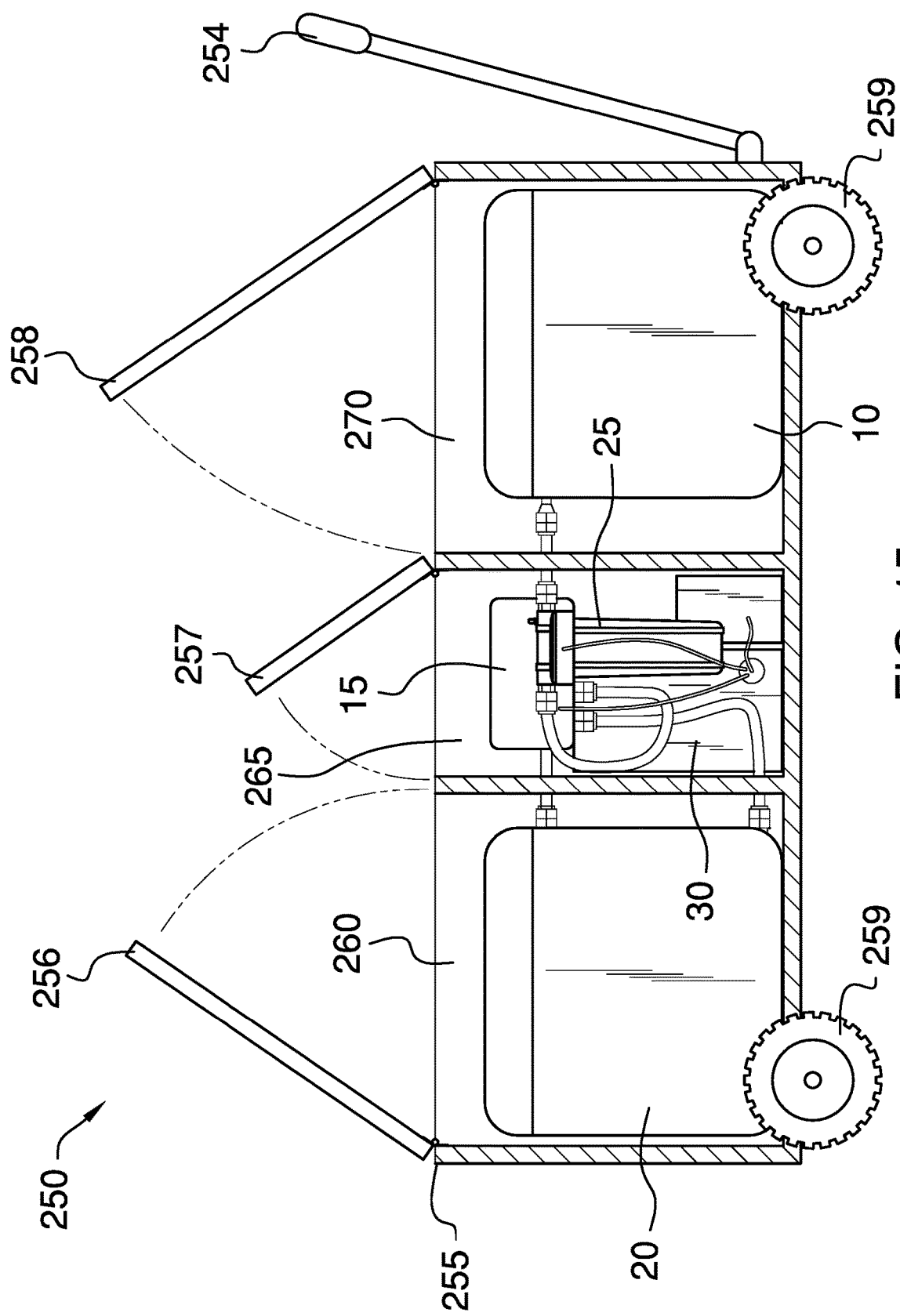
FIG. 15 is a fifth embodiment wherein the invention is provided in a horizontal orientation and contained within one housing that provides three lids and wheels for portability.

This fifth embodiment, shown in FIG. 15, is comprised of a housing 255, a first compartment 10, a second compartment 20, a pump 15, a drain 21, a rack 23, a plurality of perforations 24, a coiled pipe 12, a filter 25, and a plurality of hoses 27. The housing 255 of this fifth embodiment 250 is distinguished from the housing 205 of the fourth embodiment 200 as it is comprised of a first lid 256, a second lid 257, and a third lid 258, a first bay 260, a second bay 265, a third bay 270, a front, a back, a top, a bottom, an interior, an exterior, a plurality of wheels 259, and a handle 254.

The first lid 256, second lid 257, and third lid 258 are respectively provided above the first bay 260, second bay 265, and third bay 270. The handle 254 is provided on the front of the housing, which is shown in FIG. 15.

It is anticipated that the filter 25 may be positioned within the system so that the biocide 40 can be filtered prior to the heat exchange or alternatively positioned so that the biocide 40 is filtered after the heat exchange. In other words, the filter 25 may be placed on the inlet side or the exit side of the chilled or heated coiled pipes 12 that the biocide 40 is being pumped through.

While the embodiments of the invention have been disclosed, certain modifications may be made by those skilled in the art to modify the invention without departing from the spirit of the invention. Specifically, but not limited to, it is anticipated that a programmable controller (not shown) may be used for controlling the temperature of the biocide 40, the pressure at which it is circulated and pushed through the plurality of perforations 24 within the rack 23, as well as provide remote control over the apparatus.

The inventors claim:
1. A disinfectant apparatus, which is comprised of:
 a. a first compartment;
  wherein the first compartment provides a first lid;
  wherein a coiled pipe is provided within the first compartment;
 b. a second compartment;
  wherein the second compartment provides a second lid;
  wherein a perforated rack is provided within the second compartment;
 c. a drain;
  wherein the drain is provided in the second compartment;
 d. a pump;
  wherein the pump is coupled to the perforated rack and the coiled pipe;
 e. biocide;
  wherein the biocide is pumped through the perforated rack;
  wherein the biocide is pumped through the coiled pipe.
2. The disinfectant apparatus as described in claim 1 wherein a filter is provided to remove unwanted material from the biocide.
3. The disinfectant apparatus as described in claim 1 wherein the coiled pipe is chilled.

4. The disinfectant apparatus as described in claim 1 wherein the coiled pipe is heated.

5. The disinfectant apparatus as described in claim 4 wherein one or more heating elements are provided.

6. The disinfectant apparatus as described in claim 1 wherein a battery is provided.

7. The disinfectant apparatus as described in claim 1 wherein a controller is connected to the pump.

8. A towel disinfectant apparatus, which is comprised of:
   a. a housing;
      wherein the housing provides a top, a bottom, a front, a back, an interior, and an exterior;
      wherein a lid is provided at the top of the housing;
      wherein a door is provided on the front of the housing;
      wherein a plurality of bays is provided on the interior of the housing;
   b. a first compartment;
      wherein the first compartment is provided in the housing;
      wherein a coiled pipe is provided in the first compartment;
   c. a second compartment;
      wherein the second compartment is provided in the housing;
      wherein a perforated rack is provided within the second compartment;
      wherein a drain is provided in the second compartment;
   d. a pump;
      wherein the pump is provided in the housing;
   e. a plurality of hoses;
      wherein the plurality of hoses is provided in the housing;
      wherein the plurality of hoses connects to the rack, the second compartment, the pump, and the coiled pipe;
   f. biocide;
      wherein the biocide is pumped through the plurality of hoses, the rack, and the coiled pipe.

9. The disinfectant apparatus as described in claim 8 wherein a filter is provided within the housing.

10. The disinfectant apparatus as described in claim 8 wherein the coiled pipe is heated or chilled.

11. The disinfectant apparatus as described in claim 10 wherein one or more heating elements are provided.

12. The disinfectant apparatus as described in claim 8 wherein a battery is provided.

13. The disinfectant apparatus as described in claim 8 wherein a controller is connected to the pump.

* * * * *